United States Patent [19]
Harrison et al.

[11] Patent Number: 5,807,865
[45] Date of Patent: Sep. 15, 1998

[54] 3,3-DISUBSTITUTED PIPERIDINE DERIVATIVES AND THEIR USE AS THERAPEUTIC AGENTS

[75] Inventors: Timothy Harrison, Cambridge; Christopher John Swain, Essex, both of England

[73] Assignee: Merck Sharp & Dohme Limited, Hoddesdon, United Kingdom

[21] Appl. No.: 733,482

[22] Filed: Oct. 18, 1996

[30] Foreign Application Priority Data

Oct. 24, 1995 [GB] United Kingdom .................. 9521781

[51] Int. Cl.⁶ ..................... A61K 31/445; C07D 221/20
[52] U.S. Cl. .................. 514/278; 514/320; 514/326; 514/318; 546/15; 546/16; 546/17; 546/18; 546/19; 546/20; 546/193; 546/194
[58] Field of Search .................... 514/278, 320, 514/326, 318; 546/15, 16, 17, 18, 19, 20, 193, 194

[56] References Cited

U.S. PATENT DOCUMENTS

| | | | |
|---|---|---|---|
| 5,340,822 | 8/1994 | Emonds-Alt | 514/316 |
| 5,350,582 | 9/1994 | Emonds-alts | 544/336 |
| 5,434,158 | 7/1995 | Shah | 514/278 |
| 5,559,132 | 9/1996 | Miller | 514/329 |
| 5,589,489 | 12/1996 | Shenvi | 514/323 |
| 5,635,510 | 6/1997 | Burkholder | 514/278 |

FOREIGN PATENT DOCUMENTS

| | | |
|---|---|---|
| 0 512 901 | 11/1992 | European Pat. Off. . |
| 0 673 928 | 9/1995 | European Pat. Off. . |
| 0 723 959 | 7/1996 | European Pat. Off. . |
| 95/05377 | 2/1995 | WIPO . |

OTHER PUBLICATIONS

T. Harrison, wt al., Poster Presentation at Gordon Research Conference on Medicinal Chemistry, Colby Sawyer College, New London, New Hampshire, US (Aug. 4–9, 1996) "High Affinity, Selective Neurokinin 2 and Neurokinin 3 Receptor Antagonists from a Common Structural Template".

*Primary Examiner*—Ceila Chang
*Attorney, Agent, or Firm*—J. Eric Thies; David L. Rose

[57] ABSTRACT

The present invention relates to compounds of the formula (I)

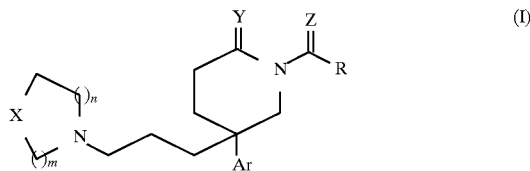

wherein X, Z, R, $R^1$, $R^2$, Ar, n and m are as defined herein which are of use in the treatment or prevention of neuropathy, asthma, osteoarthritis, rheumatoid arthritis or migraine.

12 Claims, No Drawings

3,3-DISUBSTITUTED PIPERIDINE DERIVATIVES AND THEIR USE AS THERAPEUTIC AGENTS

The invention disclosed herein is directed to certain spiro-substituted azacycles useful as tachykinin receptor antagonists. In particular, the compounds disclosed herein are antagonists at the neurokinin-2 receptor and/or the neurokinin-3 receptor.

The invention is also concerned with pharmaceutical formulations with these novel compounds as active ingredients and the use of the novel compounds and their formulations in the treatment of certain disorders including inflammatory diseases, pain, migraine, asthma, emesis and CNS disorders.

The tachykinins, substance P (SP), neurokinin A (NKA) and neurokinin B (NKB), are structurally similar members of a family of neuropeptides. Each of these is an agonist of the receptor types, neurokinin-1 receptor (NK-1), neurokinin-2 receptor (NK-2) and neurokinin-3 receptor (NK-3), which are so defined according to their unique amino acid sequence and their relative abilities to bind tachykinins with high affinity and to be activated by the natural agonists SP, NKA and NKB, respectively.

The tachykinins are distinguished by a conserved carboxyl-terminal sequence. For a review see, for instance, J. E. Maggio, *Peptides* 6(suppl. 3), 237–242.

The neurokinin receptors are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, (1983) 35, 85–141). The NK-1 and NK-2 receptor subtypes are implicated in synaptic transmission (Laneuville et al., *Life Sci.*, (1988) 42, 1295–1305).

Substance P acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science*, (1978) 199, 1359; P. Oehme et al., *Science*, (1980) 208, 305) and plays a role in sensory transmission and pain perception (T. M. Jessell, *Advan. Biochem. Psychopharmacol.* (1981) 28, 189). In particular, substance P has been shown to be involved in the transmission of pain in migraine (see B. E. B. Sandberg et al., *J. Med. Chem.*, (1982) 25, 1009), and in arthritis (Levine et al. *Science*, (1984) 226, 547–549).

In the airways, it has been indicated that NK-1 receptors are associated with microvascular leakage and mucus secretion, while NK-2 receptors regulate smooth muscle contraction. Also, it has been shown that both substance P and neurokinin A are effective in inducing airway constriction and edema. Based on such findings, it is believed that substance P and neurokinin A may be involved in the pathogenesis of neurogenic inflammation, including allergic diseases such as asthma. (Frossard et al., *Life Sci.*, (1991) 49, 1941–1953; Advenier, et al., *Biochem. Biophys. Res. Comm.*, (1992) 184(3), 1418–1424).

In experimental studies, sensory neuropeptides, especially tachykinins such as substance P and neurokinin A, can bring about many of the pathophysiological features of asthma. Neurokinin A is a very potent constrictor of human airways in vitro, and substance P causes mucus secretion in the airways. (P. J. Barnes, *Lancet*, (1986) pp242–44; D. R. Rogers et al, *Eur. J. Pharmacol*, (1989) 174, 283–86).

Inhalation of bradykinin causes bronchoconstriction in asthmatic patients but not in normal subjects (R. W. Fuller et al, *Am. Rev. Respir. Dis.*, (1987) 135, 176–80). Since the bradykinin-induced bronchoconstriction is partly opposed by anticholinergic agents and since bradykinin is only a weak constrictor of human airways in vitro, it has been suggested that the bronchoconstrictor response is partly mediated by a neural reflex. Bradykinin stimulates vagal afferent C fibers and causes bronchoconstriction in dogs (M. P. Kaufman et al, *J. Appl. Physio.*, (1980) 48, 511–17). In guinea-pig airways, bradykinin causes a bronchoconstrictor response by way of cholinergic and sensory-nerve-mediated mechanisms. (M. Ichinoe et al, *J. Pharmacol. Exp. Ther.*, (1990) 253, 594–99). Bradykinin-induced bronchoconstriction in human airways may therefore be due partly to tachykinin released from sensory nerve terminals via axon reflex mechanisms. Clinical trials have shown that a dual NK-1/NK-2 antagonist (such as FK-224) protects against bradykinin induced bronchocontriction in asthmatic patients. W. Ichinoe, et al, *The Lancet*, (1992) 340, 1248–1251).

The tachykinins have also been implicated in gastrointestinal (GI) disorders and diseases of the GI tract, such as inflammatory bowel disease, ulcerative colitis and Crohn's disease, etc. (see Mantyh et al, *Neuroscience*, (1988) 25 (3), 817–37 and D. Regoli in "Trends in Cluster Headache" Ed. F. Sicuteri et al., Elsevier Scientific Publishers, Amsterdam, 1987, pp. 85–95).

It is also hypothesized that there is a neurogenic mechanism for arthritis in which substance P may play a role (Kidd et al, "A Neurogenic Mechanism for Symmetric Arthritis" in *The Lancet,* 11 Nov., 1989 and Gronblad et al., "Neuropeptides in Synovium of Patients with Rheumatoid Arthritis and Osteoarthritis" in *J. Rheumatol.* (1988) 15(12) 1807–1810). Therefore, substance P is believed to be involved in the inflammatory response in diseases such as rheumatoid arthritis and osteoarthritis (O'Byrne et al, in *Arthritis and Rheumatisim* (1990) 33 1023–1028). Other disease areas where tachykinin antagonists are believed to be useful are allergic conditions (Hamelet et al, *Can. J. Pharmacol. Physiol.* (1988) 66, 1361–1367), immunoregulation (Lotz et al, *Science* (1988) 241, 1218–1221; Kimball et al, *J. Immunol.* (1988) 141(10), 3564–3569; and A. Perianin, et al, *Biochem. Biophys. Res. Commun.*, (1989) 161, 520) vasodilation, bronchospasm, reflex or neuronal control of the viscera Mantyh et al, *PNAS* (1988) 85, 3235–3239) and, possibly by arresting or slowing β-amyloid-mediated neurodegenerative changes (Yankner et al, *Science*, (1990) 250, 279–82) in senile dementia of the Alzheimer type, Alzheimer's disease and Down's Syndrome. Substance P may also play a role in demyelinating diseases such as multiple sclerosis and amyotrophic lateral sclerosis [J. Luber-Narod et. al, poster presented at *C.I.N.P. XVIIIth Congress,* 28th Jun.–2nd Jul., 1992]. Antagonists selective for the substance P and/or the neurokinin A receptor may be useful in the treatment of asthmatic disease (Frossard et al, *Life Sci.*, (1991) 49, 1941–1953; Advenier, et al, *Biochem. Biophys. Res. Commun.*, (1992) 184(3), 1418–1424). These antagonists may also be useful in the treatment of emesis (see C. Bountra et al, *Eur. J. Pharmacol.*, (1993) 249, R3–R4; and F. D. Tattersall et al, *Eur. J. Pharmacol.*, (1993) 250, R5–R6.

The localisation of tachykinins and neurokinin receptor subtypes within the striatum is also heterogeneous. NKB immunoreactive fibres are colocalised within GABA containing neurones that project to the palladium but not the substantia nigra pars reticulata, whereas the SP containing neurones project principally to the substantia nigra pars reticulata (see J. M. Burgunder & W. S. Young, *Neurosci.* (1989) 32, 323–335). Activation of tachykinin receptors in the straitum modulates the release of neurotransmitters including acetylcholine and dopamine (see L. Tremblay et al, *Proc. Natl. Acad. Sci. USA* (1992) 89, 11214–11218). Interestingly in that study the release of dopamine by [Pro⁷]NKB (NK-3) in the matrix compartment was insensitive to tetrodotoxin suggesting a presynaptic localisation of NK-3 receptors.

This hypothesis is further supported by the finding that the NKB-induced stimulation of acetylchlorine release in rat striatum is reduced by both TTX and by lesions of the nigrostriatal pathway, and is consistent with the presence of NK-3 receptors on dopamine cell bodies of the striatonigral and mesolimbic pathways (see E. Arenas et al, *J. Neurosci.* (1991) 11(8), 2332–2338; and K. D. Keegan et al, *Br. J. Pharmacol.*, (1992) 105, 3–5.

We have found that tachykinin receptor subtype on presumed dopamine neurones of the rat ventral tegmental area are a NK-3 and not a NK-1 or NK-2 receptor subtype. These data suggest that NK-3 receptors mediate the principal excitatory influence of tachykinins on mesolimbic dopamine neurones; however the role of receptors on afferent projections to the VTA and the relative tone of neuropeptide-containing fibres may have a more significant influence over their function.

Binding studies have shown NK-3 receptors to be present in brain slices from several species eg rat, mouse and guinea-pig, however, Dietl & Palacios, using [$^{125}$I]-labelled Bolton Hunter (BH) eledoisin reported an absence of NK3-receptors in primate and human brain. The human NK-3 receptor was cloned from human brain mRNA, indicating that the protein is expressed in this tissue (see Huang, et al, *Biochem. Biophys. Res. Commnun.*, (1992) 184, 996–972). However, the cloned human NK-3 receptor has lower affinity for eledoisin than the rat receptor and this probably explains the apparent absence of NK-3-binding sites in human brain when [$^{125}$I]-BH-eledoisin is used as the ligand. Indeed, using [$^{3}$H]-senktide Guard & Watson readily demonstrated the presence of NK-3-binding sites in primate brain (see M. M. Dietl & J. M. Palacios, *Brain Res.*, (1991) 539, 211–222; G. Buell et al, *Febs Letts.*, (1992) 299, 90–95; and S. Guard & S. P. Watson, *Neurochem. Int.* (1991) 18, 149–165).

Interestingly, infusion of senktide (an NK-3 receptor agonist) by microdialysis in the substantia nigra and VTA of the rat caused behavioural responses characteristic of the activation of dop aminergic pathways and this effect was different with age. This observation implies that neurokinin receptors may play a role in central dop aminergic disorders, particularly those such as Parkinsonism which are more prelevant in advanced age (see A. J. Stoessl et al, *Brain Res.*, (1993) 632, 21–28).

The present invention provides compounds of the formula (I)

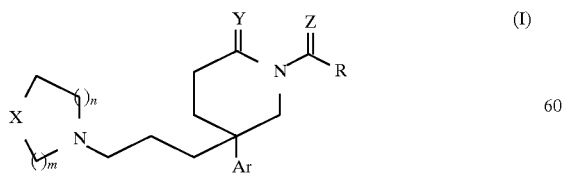

wherein
m is zero, 1 or 2;
n is 1, 2 or 3, with the proviso that the sum of m+n is 1 to 4;

X represents

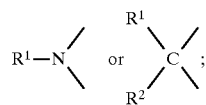

one of Y and Z represents =O whilst the other represents two hydrogen atoms;

Ar represents unsubstituted phenyl; phenyl substituted by 1, 2 or 3 substituents selected from hydroxy, cyano, halogen, trifluoromethyl,$C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy; thienyl; benzothienyl; naphthyl; unsubstituted indolyl; or indolyl substituted on the nitrogen atom by a $C_{1-4}$alkyl group;

R represents unsubstituted phenyl or phenyl substituted by 1, 2 or 3 substituents selected from hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy;

$R^1$ represents hydrogen; $C_{1-6}$alkyl; $C_{1-6}$alkyl substituted by 1 or 2 substituents selected from hydroxy, —$OR^3$, oxo, —$NHCOR^3$, —$NR^3R^4$, cyano, halogen, trifluoromethyl, unsubstituted phenyl, and phenyl substituted by 1 or 2 substituents selected from hydroxy, cyano, halogen and trifluoromethyl; unsubstituted phenyl; phenyl substituted by 1, 2 or 3 substituents selected from hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl and —$C(O)R^3$; unsubstituted aryl; aryl substituted by 1, 2 or 3 substituents selected from hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl and —$C(O)R^3$; or a saturated heterocyclic ring of 4, 5 or 6 ring atoms which ring contains 1 or 2 nitrogen atoms, one of which may be at the point of attachment to the remainder of the molecule, and optionally containing in the ring an oxygen atom, which ring is substituted on any available nitrogen atom by a group $R^5$ and which ring may be further substituted by a group selected from hydroxy$C_{1-4}$alkyl, $C_{1-4}$alkoxy$C_{1-4}$alkoxy, oxo and $COR^3$, and which ring may have fused thereto a phenyl ring, wherein the phenyl ring may be substituted by 1 or 2 substituents selected from hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$; $R^2$ represents $C_{1-6}$alkyl hydroxy$C_{1-6}$alkyl, hydroxy, $OR^3$, halogen, trifluoromethyl, nitro, cyano, —$NR^3R^4$, —$NHCOR^3$, —$NR^3COR^4$, —$NHCO_2R^3$, —$NR^3CO_2R^4$, —$NHS(O)_pR^3$, —$NR^3S(O)_pR^4$, —$CONR^3R^4$, —$COR^3$, —$CO_2R^3$ or —$S(O)_pR^3$; or $R^1$ and $R^2$ are joined together to form a 5- or 6-membered non-aromatic ring which may contain in the ring 1 or 2 groups of the formula $NR^5$, which ring is optionally substituted by an oxo group and which ring may be substituted by, or have fused thereto, a phenyl group, wherein the phenyl ring may be substituted by 1 or 2 substituents selected from hydroxy, cyano, —$C(O) NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$; $R^3$ and $R^4$ each independently represent hydrogen; unsubstituted $C_{1-6}$alkyl; $C_{1-6}$alkyl substituted by 1 or 2 substituents selected from unsubstituted phenyl, hydroxy, oxo, cyano, $C_{1-4}$alkoxy and trifluoromethyl; $C_{1-6}$alkoxy; unsubstituted phenyl; or phenyl substituted by 1, 2 or 3 substituents selected from hydroxy, $C_{1-4}$alkyl, cyano, halogen, trifluoromethyl;

or the group —$NR^3R^4$ represents a saturated or partially saturated heterocyclic ring of 4 to 7 ring atoms, which ring may optionally contain in the ring one oxygen or sulphur atom or a group selected from $NR^5$, $S(O)$ or $S(O)_2$ and which ring may be optionally substituted by one or two groups selected from hydroxy$C_{1-4}$alkyl, $C_{1-4}$alkoxy$C_{1-4}$alkyl, oxo, $COR^6$ or $CO_2R^6$;

$R^5$ represents hydrogen, $C_{1-4}$alkyl, —$S(O)_2C_{1-4}$alkyl, —$C(O)R^3$, unsubstituted phenyl or benzyl;

$R^6$ represents hydrogen or $C_{1-4}$alkyl; and p1 is zero, 1 or 2;

or a pharmaceutically acceptable salt thereof.

When used herein the term "halogen" means fluorine, chlorine, bromine and iodine. The most apt halogen are fluorine and chlorine of which fluorine is preferred.

When used herein the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The term "alkenyl" as a group or part of a group means that the group is straight or branched and contains at least one double bond. Examples of suitable alkenyl groups include vinyl and allyl.

The term "alkynyl" as a group or part of a group means that the group is straight or branched and contains at least one triple bond. An example of a suitable alkynyl group is propargyl.

Suitable cycloalkyl and cycloalkyl-alkyl groups include cyclopropyl, cyclobutyl, cyclopentyl, cyclohexyl, cyclopropylmethyl and cyclobutylmethyl.

When used herein the term "heteroaryl" represents a heteroaromatic ring including furanyl, thienyl, pyrrolyl, oxazolyl, thiazolyl, isoxazolyl, isothiazolyl, imidazolyl, pyrazolyl, triazolyl, oxadiazolyl, thiadiazolyl, tetrazolyl, pyridyl, pyrazinyl, pyrimidyl, benzofuranyl, benzthienyl, indolyl, benzimidazolyl, benzoxazolyl and quinolyl.

Where the group $NR^3R^4$ forms a saturated heterocylic ring of 4 to 7 ring atoms which may optionally contain in the ring one oxygen or sulphur atom or a group selected from $NR^5$, $S(O)$ or $S(O)_2$, suitable heterocyclic groups include azetidinyl, pyrrolidino, piperidino, homopiperidino, piperazino, N-methylpiperazino, morpholino and thiomorpholino.

Suitable substituents on the saturated heterocyclic ring include $CH_2OH$, $CH_2OCH_3$, oxo, CHO, $CO_2H$, $CO_2CH_3$, and $CO_2CH_2CH_3$.

A preferred class of compounds of formula (I) is that wherein the sum of m+n is 3. In particular, m is preferably 2. In particular, n is preferably 1.

A preferred group represented by X is

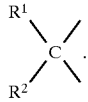

Ar preferably represents unsubstituted phenyl or phenyl substituted by 1, 2 or 3 substituents selected from hydroxy, cyano, halogen, triflouromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy. Preferred substituents are halogen atoms, most especially chlorine atoms. In particular, Ar represents phenyl substituted by two substituents. Preferably Ar represents a 3,4-disubstituted phenyl ring.

R preferably represents unsubstituted phenyl or phenyl substituted by 1, 2 or 3 substituents selected from hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy. Preferred substituents are halogen atoms, most especially chlorine atoms. In particular, R represents an unsubstituted phenyl ring.

$R^1$ preferably represents an unsubstituted phenyl group or a saturated heterocyclic ring of 5 ring atoms which ring contains 1 or 2 nitrogen atoms, one of which is at the point of attachment to the remainder of the molecule, which ring is substituted on any available nitrogen atom by a group $R^5$, preferably where $R^5$ is hydrogen, and which ring is preferably substituted by an oxo group, and which ring has fused thereto a phenyl ring, wherein the phenyl ring may be substituted by 1 or 2 substituents selected from hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$. Preferably the phenyl ring is unsubstituted.

$R^2$ preferably represents hydrogen or —$COR^3$, where $R^3$ represents $C_{1-6}$alkyl, in particular $C_{1-3}$alkyl, especially methyl.

A further preferred class of compound of formula (I) is that wherein $R^1$ and $R^2$ are joined together to form a 5-membered non-aromatic ring which may contain in the ring 1 or 2 groups of the formula $NR^5$, which ring is optionally substituted by an oxo group and which ring may be substituted by, or have fused thereto, a phenyl group, wherein the phenyl ring may be substituted by 1 or 2 substituents selected from hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$. Preferably the phenyl ring, where present, is unsubstituted.

Where present, $R^3$ and $R^4$ each independently preferably represent hydrogen or $C_{1-6}$alkyl.

$R^5$ preferably represents hydrogen, $C_{1-4}$alkyl, —$S(O)_2C_{1-4}$alkyl or unsubstituted phenyl. In particular, $R^5$ is preferably hydrogen, —$S(O)_2CH_3$ or phenyl.

From the foregoing, it will be appreciated that a particularly preferred sub-group of compounds according to the present invention are those of formula (Ia):

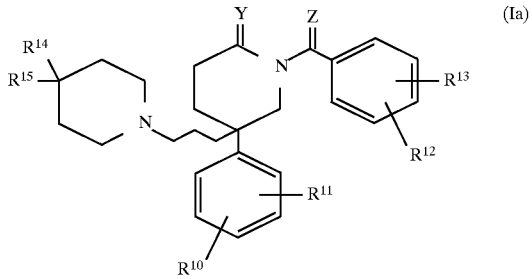

(Ia)

wherein $R^{10}$, $R^{11}$, $R^{12}$ and $R^{13}$ are hydrogen or halogen atoms;

$R^{14}$ is an unsubstituted phenyl group or a saturated heterocyclic ring of 5 ring atoms which ring contains 1 or 2 nitrogen atoms, one of which is at the point of attachment to the remainder of the molecule, which ring is substituted on any available nitrogen atom by a group $R^5$, and which ring may be substituted by an oxo group, and which ring has fused thereto a phenyl ring, wherein the phenyl ring may be substituted by 1 or 2 substituents selected from hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$;

$R^{15}$ is —COR$^3$, where R$^3$ is C$_{1-6}$alkyl;

or $R^{14}$ and $R^{15}$ are joined together to form a 5-membered non-aromatic ring which may contain in the ring 1 or 2 groups of the formula NR$^5$, which ring is optionally substituted by an oxo group and which ring may be substituted by, or have fused thereto, a phenyl group, wherein the phenyl ring may be substituted by 1 or 2 substituents selected from hydroxy, cyano, —C(O)NR$^3$R$^4$, —NR$^3$R$^4$, —NR$^3$COR$^4$, halogen, trifluoromethyl, C$_{1-4}$alkyl, —S(O)$_p$C$_{1-4}$alkyl, and —C(O)R$^3$; and Y and Z are as defined in relation to formula (I);

or a pharmaceutically acceptable salt thereof.

A preferred class of compound of formula (Ia) is that wherein R$^{10}$ and R$^{11}$ each represent chlorine atoms, R$^{12}$ and R$^{13}$ each represent hydrogen atoms, R$^{14}$ represents unsubstituted phenyl, and R$^{15}$ represents —COCH$_3$, or R$^{14}$ and R$^{15}$ are joined together to form a 5-membered non-aromatic ring which may contain in the ring 1 or 2 groups of the formula NR$^5$, which ring is optionally substituted by an oxo group and which ring may be substituted by, or have fused thereto, an unsubstituted phenyl group, wherein R$^5$ represents hydrogen, —S(O)$_2$CH$_3$ or phenyl.

Particularly preferred compounds of formula (I) are those wherein m is 2, n is 1 and X represents:

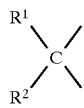

to give a group of the formula:

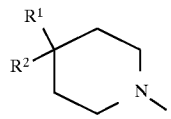

of which preferred examples are selected from:

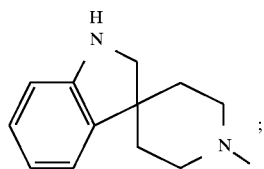

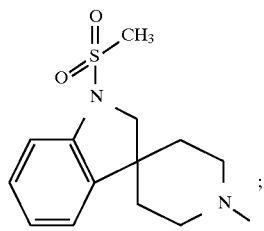

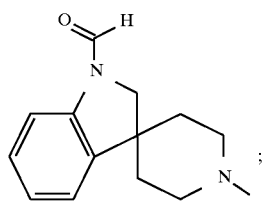

-continued

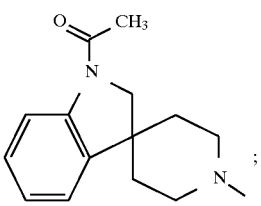

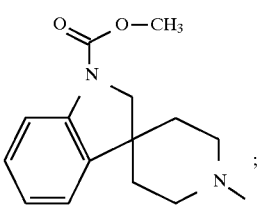

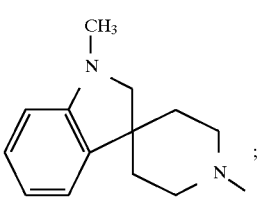

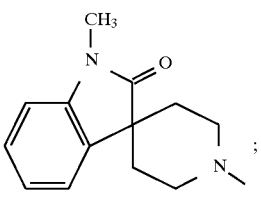

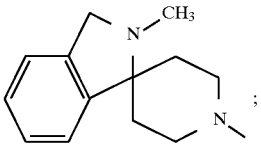

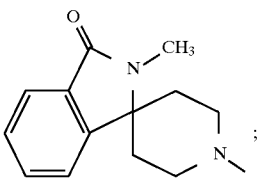

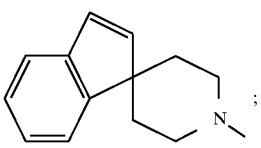

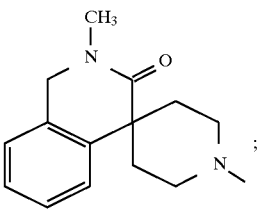

-continued
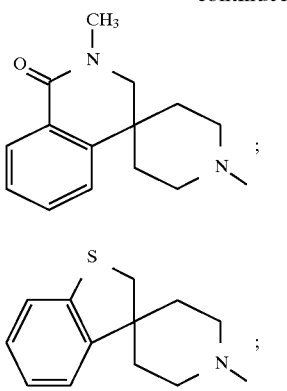
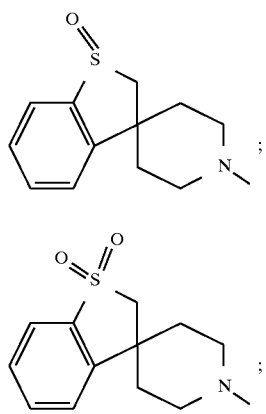
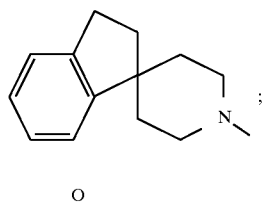
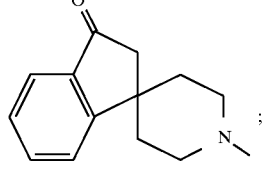
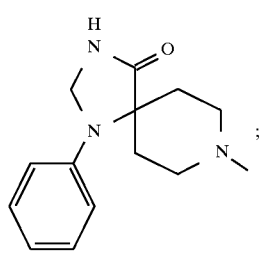
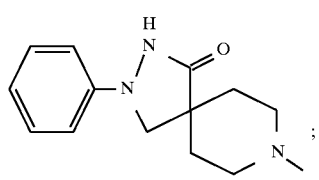
-continued
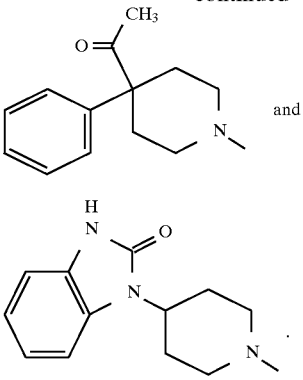
wherein each phenyl ring may be substituted by 1 or 2 substituents selected from hydroxy, cyano, —C(O)NR$^3$R$^4$, —NR$^3$R$^4$, —NR$^3$COR$^4$, halogen, trifluoromethyl, C$_{1-4}$alkyl, —S(O)$_p$C$_{1-4}$alkyl and —C(O)R$^3$;, where R$^3$, R$^4$ and p are as previously defined.
Particularly preferred groups represented by
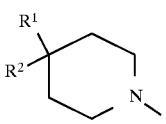
include:
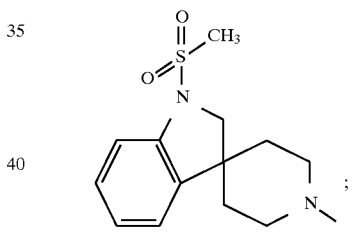
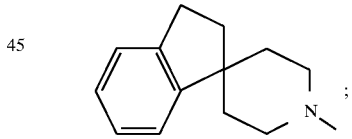
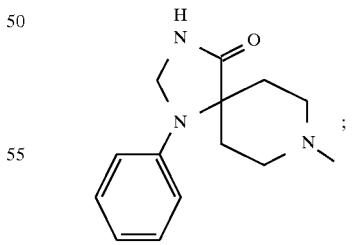
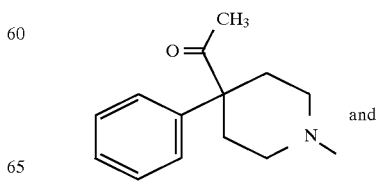

-continued

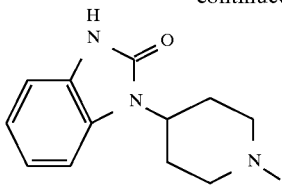

Specific compounds within the scope of the present invention include:

5-[3-{4,4-(N-sulfonamidomethyl-3,3-indolyl) piperidino}propyl]-5-[3,4-diphenyl]-1 -benzylpiperidin-2-one;

5-[3-{4-(2-keto-1-benzimidazolinyl)-piperidino}propyl]-5-[3,4-dichlorophenyl]-1-benzylpiperidin-2-one;

5-[3-{4-acetyl-4-phenyl-piperidino}propyl]-5-[3,4-dichlorophenyl]-1-benzylpiperidin-2-one;

5-[3-{1-phenyl-1,3,8-triazaspiro[4.5]decan-4-one}propyl]-5-[3,4-dichlorophenyl]-1-benzylpiperidin-2-one;

5-[3-{4,4-(N-sulfonamidomethyl-3,3-indolyl) piperidino}propyl]-5-[3,4-diphenyl]-1-benzoylpiperidine;

5-[3-{4-(2-keto-1-benzimidazolinyl)-piperidino}propyl]-5-[3,4-dichlorophenyl]-1-benzoylpiperidine;

5- [3-{4-acetyl-4-phenyl-piperidino}propyl]-5-[3,4-dichlorophenyl]-1-benzoylpiperidine;

5-[3-{1-phenyl-1,3,8-triazaspiro[4.5]decan-4-one}propyl]-5-[3,4-dichlorophenyl]-1-benzoylpiperidine;

5-[3-{4,4-(1,1-indanyl)piperidino}propyl]-5-[3,4-diphenyl]-1-benzoylpiperidine;

and pharmaceutically acceptable salts thereof

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts. e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention may have one or more asymmetric centres, and may accordingly exist both as enantiomers and as diastereoisomers. It is to be understood that all such isomers and mixtures thereof are encompassed within the scope of the present invention.

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0. 1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.0 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

As may be appreciated by those of skill in the neurokinin art, it is generally important to treat a patient with a neurokinin mediated disease, with an antagonist that is specific for the neurokinin receptors(s) mediating the disease. Thus a patient suffering from any of the diseases mediated by neurokinin-1 receptors, is generally most advantageously treated with a compound that is a potent antagonist of neurokinin-1, but is at most a weak antagonist of neurokinin-3. Even where antagonism of both neurokinin-1 and neurokinin-2 is desired, it is generally advantageous to avoid significant antagonism of neurokinin-3. Similarly, a patient suffering from any of the diseases mediated by neurokinin-3, is generally most advantageously treated with a compound that is a potent antagonist of neurokinin-3, but is at most a weak antagonist of neurokinin-1.

Accordingly, in a further embodiment of the present invention, the compounds of formula (I) are useful as a diagnostic tool for assessing the degree to which neurokinin-2 and/or neurokinin-3 receptor activity (normal, overactivity or underactivity) is implicated in a patient's symptoms. In this regard a compound of formula (I) is used as an antagonist of the activity, for example including but not restricted to tachykinin agonist-induced inositol phosphate turnover or electrophysiological activation, of a cell sample obtained from a patient. Comparison of such activity in the presence or absence of a compound of formula I will disclose the degree of NK-2 and/or NK-3 receptor involvement in the mediation of agonist effects in that tissue.

Similarly, in another embodiment of the present invention, the compounds of formula (I) are useful in assessing the degree to which a selected pharmacological effect, as measured either in vitro or in vivo, is due to activation of the NK-2 and/or NK-3 receptor. In this instance the assays are performed in the presence or absence of a compound of formula (I), and comparison of the results will disclose the degree of NK-2 and/or NK-3 receptor involvement.

The compounds of formula I are useful in the prevention and treatment of a wide variety of clinical conditions (as detailed in this specification) which are characterized by overstimulation of the tachykinin receptors, in particular NK-2 and NK-3.

The compounds of formula (I) are particularly useful in the treatment of diseases or conditions that are advantageously treated by concomitant antagonism of both NK-1 and NK-3 receptors or NK-1, NK-2 and NK-3 receptors. These diseases include neuropathy, such as diabetic or peripheral neuropathy and chemotherapy-induced neuropathy; asthma; osteoarthritis; rheumatoid arthritis; and migraine.

Other conditions include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; central dop aminergic disorders, including Parkinsonism; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic and chemotherapy-induced neuropathy, and postherpetic and other neuralgias; neuronal damage, such as cerebralischemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed, post-operative, late phase or anticipatory emesis such as emesis induced by chemotherapy, radiation, toxins, viral or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, dental pain and that attributable to or associated with any of the foregoing conditions, especially the transmission of pain in migraine. Hence the compounds of the present invention are readily adapted to therapeutic use for the treatment of physiological disorders associated with the overstimulation of the tachykinin receptors, in particular the NK-2 and/or NK-3 receptors, and as neurokinin-2 and/or neurokinin-3 antagonists for the control and/or treatment of any of the aforementioned clinical conditions in mammals, including humans.

The compounds of formula (I) are also of value in the treatment of a combination of the above conditions, in particular in the treatment of combined post-operative pain and post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABAs receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially neurokinin-A and/or neurokinin-B.

The present invention also provides a method for the the treatment or prevention of physiological disorders associated with an excess of tachykinins, especially neurokinin-A and/or neurokinin-B, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination. Suitable $\beta_2$-agonists include, but are not limited to, terbutaline (bambuterol), bitolterol, carbuterol, clenbuterol, dopexamine, formoterol, mabuterol, pirbuterol, procaterol, ritodrine, broxaterol, cimaterol, salbutamol (albuterol) and salmeterol.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270, 324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$, agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to one general process, (A), compounds of formula (I) may be prepared from a compound of formula (II)

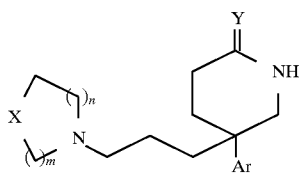

(II)

wherein Ar, X, Y, m and n are as defined in relation to formula (I), by reaction with a compound of the formula (III)

(III)

wherein R and Z are as defined in relation to formula (I) and LG represents a leaving group such as a halogen atom or an alkyl- or aryl-sulphonyloxy group, e.g. chlorine, bromine or iodine or a methylsulphonate or p-toluenesulphonate group, in the presence of a base.

For compounds wherein Y is two hydrogen atoms and Z is oxygen, suitable bases include organic bases such as tertiary amines, e.g. triethylamine, and inorganic bases such as alkali metal carbonates, e.g. sodium carbonate or potassium carbonate. Conveniently, the reaction is effected in a suitable organic solvent, such as dimethylformamide, acetonitrile or dichloromethane, conveniently at a temperature between room temperature and 100° C.

For compounds wherein Y is oxygen and Z is two hydrogen atoms, suitable bases include alkali metal hydrides, e.g. sodium hydride. Conveniently, the reaction is effected in a suitable organic solvent such as an ether, e.g. tetrahydrofuran, conveniently at a temperature between room temperature and 100° C.

According to another process, (B), compounds of formula (I) may be prepared from compounds of formula (IV)

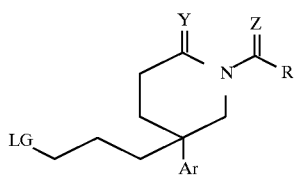

(IV)

wherein Ar, R Y and Z are as defined in relation to formula (I) and LG is as previously defined, by reaction with an amine of formula (V)

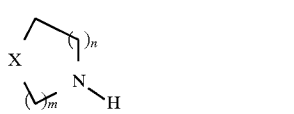

(V)

wherein X, m and n are as defined in relation to formula (I), in the presence of a base.

Suitable bases include organic bases such as tertiary amines, e.g. triethylamine, and inorganic bases such as alkali metal carbonates, e.g. sodium carbonate or potassium carbonate.

Conveniently, the reaction is effected in a suitable organic solvent, such as dimethylformamide, acetonitrile or dichloromethane, conveniently at a temperature between room temperature and 100° C.

Compounds of formula (II) may be prepared from compounds of formula (VI)

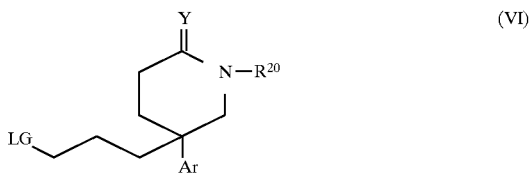

(VI)

wherein Ar and Y are as defined in relation to formula (I), LG is as previously defined, and $R^{20}$ is a suitable amine protecting group, such as an alkoxycarbonyl group, for example, tert-butoxycarbonyl, by reaction with an amine of formula (V) according to the method of process (B) above, followed by removal of any protecting group where present.

Compounds of formula (IV) may be prepared from compounds of formula (VII)

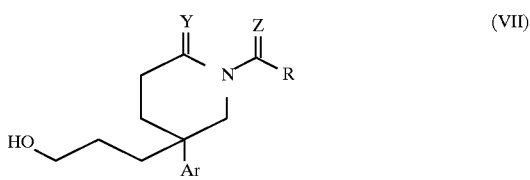

(VII)

by conventional methodology. For instance, where the desired leaving group is a halogen atom, by reaction with a corresponding halogen acid, such as hydrogen bromide or hydrogen iodide. Where the leaving group is an alkyl- or aryl-sulphonyloxy group, the compound of formula (VII) may be reacted with, for example, methanesulfonyl chloride or p-toluenesulfonyl chloride.

Alternatively, compounds of formula (IV) may be prepared by the reaction of a compound of formula (VIII)

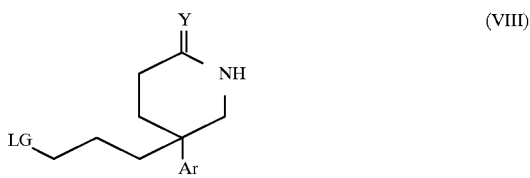

(VIII)

with a compound of formula (II) according to the method of process (A).

Compounds of formula (VII) may be prepared by the reaction of a compound of formula (IX)

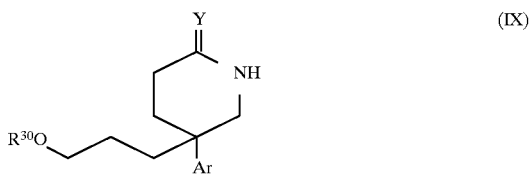

(IX)

where $R^{30}$ is a suitable hydroxy protecting group, for example, tetrahydropyran, with a compound of formula (II) according to the method of process (A), above, followed by removal of any protecting group where present.

Compounds of formula (IX) in which Y is two hydrogen atoms may be prepared by reduction of the corresponding compound of formula (IX) in which Y is an oxygen atom. Suitable reducing agents include hydrides such as lithium aluminium hydride in a suitable solvent, for example, tetrahydrofuran, conveniently at a temperature between room temperature and 100° C., for example, at about 60° C.

Alternatively, compounds of formula (IX) in which Y is two hydrogen atoms may be prepared in a two-step reaction from a compound of formula (X)

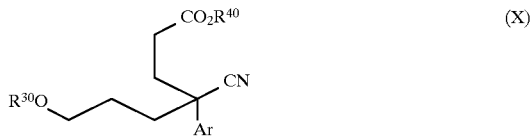

wherein $R^{30}$ is a suitable hydroxy protecting group as previously defined and $R^{40}$ is a $C_{1-6}$alkyl group, espeically an ethyl group. Firstly the compound of formula (X) is reduced using, for example, lithium aluminium hydride as described above. The resulting compound of formula (Xa)

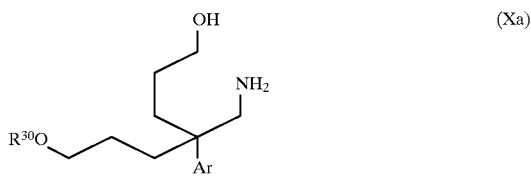

is then cyclized by converting the alcohol group to a leaving group using, for example, triphenyl phosphine, followed by the addition of diethyl azodicarboxylate (DEAD) in a suitable organic solvent, for example, dichloromethane, to complete the cyclization, this method being based upon that described by R. C. Bernotas and R. V. Cube in *Tetrahedron Letters* (1990) 91, 161–164.

Compounds of formula (IX) in which Y is an oxygen atom may also be prepared from a. corresponding compound of formula (X), by hydrogenation in the presence of an excess of Raney™ nickel. A suitable solvent for this reaction is a mixture of ethanol and ammonia.

Compounds of formula (X) may be prepared from a compound of formula (XI)

by a Michael addition using a compound of the formula $H_2C=CHCO_2R^{40}$ and a suitable base, preferably, N-benzyltrimethylammonium hydroxide (Triton B™).

Compounds of formula (XI) may be prepared by the alkylation of a compound of formula (XII) with a compound of formula (III)

wherein Ar, $R^{30}$ and LG are as previously defined, using conventional conditions, for example, using a base such as sodium hydride in a suitable solvent such as tetrahydrofuran, preferably at a temperature between −25° C. and room temperature.

Compounds of formulae (III), (V), (XII) and (XIII) are commercially available, or may be prepared from commercially available starting materials using conventional procedures well known to those skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

In particular, amino moieties may be protected by, for example, the formation of alkoxycarbonyl derivatives, e.g. tert-butoxycarbonyl and trichloroethoxycarbonyl, or benzyl, trityl or benzyloxycarbonyl derivatives. Subsequent removal of the protecting group is achieved by conventional procedures thus, for example, tert-butoxycarbonyl, benzyl or benzyloxycarbonyl groups may be removed by hydrogenolysis in the presence of a catalyst e.g. palladium; a trichloroethoxycarbonyl group may be removed with zinc dust; and a trityl group may be removed under acidic conditions using standard procedures.

Where hydroxyl groups require protection, this may be effected by the formation of esters or trialkylsilyl, tetrahydropyran or benzyl ethers. Such derivatives may be deprotected by standard procedures thus, for example, a tetrahydropyran ether derivative may be deprotected using hydrochloric acid in methanol.

The following Examples illustrate the preparation of compounds according to the present invention:

INTERMEDIATE 1

3,4-Dichlorotetrahydropyranyloxypropyl-α-benzeneacetonitrile 3,4-Dichlorophenylacetonitrile (52.0 g, 0.280 mol) and 3-bromopropoxy-tetrahydropyrane (68.6 g, 1.1 eq) were mixed in tetrahydrofuran (350 ml) and cooled to -20° C. Sodium hydride (60% in oil, 30 g, 2.7 eq) was added during 25 minutes. The solution was allowed to warm to room temperature and stirred for 2 hours. The reaction was quenched carefully with water and partitioned with ethyl acetate and the aqueous phase was extracted with ethyl acetate (×2). The combined organic phase was washed with water (×2), brine (×1) and dried (MgSO$_4$). The solvent was evaporated and the residue was purified by flash chromatography using petroleum ether/dichloromethane (gradient 100:0 to 0:100) as eluant to provide the title compound as a viscous yellow oil (77.0 g, 84% yield).

$^1$H NMR (250 MHz, CDCl$_3$): δ 7.48 (2H, m) 7.20 (1H, dd, J$_1$=8.29 Hz, J$_2$=2.17 Hz) 4.55 (1H, t, J=1.74 Hz) 3.92–3.74 (2H, m) 3.55–3.39 (2H, m) 2.07–1.97 (2H, m) 1.83–1.71 (4H, m) 1.55 (4H, m) 1.26 (1H, t, J=14.29 Hz). m/z (ES+) 327/329 due to chlorine isotope pattern.

INTERMEDIATE 2

4-[3-Tetrahydropyranyloxypropyl]4-cyano4-[3,4-dichlorophenyl]-ethylbutanoate

The nitrile (Intermediate 1) (30.15 g, 0.0919 mol) was dissolved in 1,4-dioxane (200 ml). Ethyl acrylate (17.56 g, 1.7 eq) and Triton B™ (5 ml, 40 wt %, methanol) were added and the solution was stirred at 80° C. for 29 hours at room temperature. The reaction was quenched with ammonium chloride and extracted with diethyl ether (×2). The combined organic phase was washed with water (×2), brine (×1) and dried (MgSO$_4$). The solvent and unreacted ethyl acrylate were evaporated to provide the title compound as a viscous yellow oil (37.4 g, 95% yield).

$^1$H NMR (250 MHz, CDCl$_3$): δ 7.48 (2H, m) 7.26 (1H, dd, J$_1$=8.29 Hz, J$_2$=2.17 Hz) 4.51 (1H, dt, J$_1$=10.23 Hz, $J_2$=3.21 Hz) 4.17–4.03 (2H, m) 3.86–3.65 (2H, m) 3.51–3.32 (2H, m) 2.54–1.96 (6H, m) 1.77–1.66 (4H, m) 1.51 (4H, m) 1.24 (3H, m). m/z (ES+) 428/430 due to chlorine isotope pattern

INTERMEDIATE 3

5-[3-Tetrahydropyranyloxypropyl]-5-[3,4-dichlorophenyl]-piperidin-2-one

The ester nitrile (Intermediate 2) (26.66 g, 0.062 mol) was dissolved in ethanol (140 ml) and ammonia (22 ml). Raney™ nickel catalyst was added (8 "scoops") and the solution was hydrogenated at 40 psi for 48 hours (the hydrogen was recharged several times the first couple of hours). The solution was filtered, keeping the catalyst wet at all times, the solvent was evaporated under high vacuum and the residue was purified by flash chromatography using ethyl acetate/methanol (gradient 100:0 to 80:20) as eluant to provide the title compound as a clear yellow viscous oil (18.3 g, 76% yield).

$^1$H NMR (360 MHz, CDCl$_3$): δ 7.41 (2H, m) 7.15 (1H, dd, $J_1$=8.45 Hz, $J_2$=2.3 Hz) 7.10 (1H, s) 4.45 (1H, dt, $J_1$=10.23 Hz, $J_2$=3.21 Hz) 3.77 (1H, m) 3.69–3.56 (2H, m) 3.45 (1H, m) 3.36 (1H, dd, $J_1$=12.7 Hz, $J_2$=undetectable) 3.25 (1H, m) 2.16–2.04 (2H, m) 1.88–1.79 (2H, m) 1.65 (2H, m) 1.51 (4H, m) 1.33–1.18 (3H, m).

INTERMEDIATE 4

5-[3-Tetrahydropyranyloxypropyl]-5-[3,4-dichlorophenyl]-1-benzylpiperidin-2-one The piperidinone (Intermediate 3) (4.43 g, 0.010 mol) was dissolved in tetrahydrofuran (40 ml). Sodium hydride (60% in oil, 0.44 g, 1.1 eq) and benzyl bromide (1.88 g, 1.1 eq) were added and the mixture stirred at room temperature for 16 hours. The reaction was quenched with water and extracted with ethyl acetate (×3). The combined organic phase was washed with water (×1), brine (×1) and dried (MgSO$_4$). The solvent was evaporated and the residue was purified by flash chromatography using ethyl acetate/petroleum ether (50:50) as eluant to provide the title compound.

$^1$H NMR (250 MHz, CDCl$_3$) (this spectrum only contains very broad peaks so in the following only the chemical shifts and the integrations are given) δ 7.34 (6H) 7.08 (1H) 6.80 (1H) 4.86 (1H) 4.42 (1H) 3.75 (1H) 3.52 (3H) 3.22 (2H) 2.44 (1H) 2.12 (2H) 1.67 (4H) 1.51 (4H) 1.17 (3H).

INTERMEDIATE 5

5-[3-Hydroxypropyl]-5-[3,4-dichlorophenyl]-1-benzylpiperidin-2-one

The THP protected piperidinone (Intermediate 4) (4.11 g, 8.65 mmol) was deprotected by stirring with 3M hydrochloric acid/methanol (50 ml) for 2 hours. The solvent was evaporated and the residue was redissolved in ethyl acetate and washed with sodium bicarbonate (×1), brine (×1) and dried (MgSO$_4$). The solvent was evaporated to afford the title compound as a yellow oil which was used without further purification.

INTERMEDIATE 6

5-[3-Methanesulfonyloxypropyl]-5-[3,4-dichlorophenyl]-1-benzylpiperidin-2-one The deprotected piperidinone (Intermediate 5) (3.28 g, 8.39 mmol) was dissolved in dichloromethane (25 ml) on a water bath. Triethylamine (1.27 g, 1.5 eq) was added followed by methanesulfonyl chloride (1.05 g, 1.1 eq). The mixture was stirred for 1.5 hours at room temperature and then quenched with sodium bicarbonate. The aqueous phase was extracted with dichloromethane (×2) and the combined organic phase was washed with water (×1), brine (×1) and dried MgSO$_4$). The solvent was evaporated and the residue was purified by flash chromatography using ethyl acetate/petroleum ether (gradient 50:50 to 100:0) as eluant to provide the title compound as a clear gum.

$^1$H NMR (250 MHz, CDCl$_3$): δ 7.38–7.26 (6H, m) 7.08 (1H, d, J=2.28 Hz) 6.78 (1H, dd, $J_1$=8.44 Hz, $J_2$=2.28 Hz) 4.87 (1H, d, J=14.31 Hz) 4.36 (1H, d, J=14.3 Hz) 4.02 (1H, t, J=6.15 Hz) 3.54 (1H, d, J=12.02 Hz) 3.27 (1H, d, J=12.02 Hz) 2.94 (3H, s) 2.51–2.41 (1H, m) 2.26–1.97 (3H, m) 1.84–1.57 (2H m) 1.36–1.24 (2H, m).

INTERMEDIATE 7

5-(3-Tetrapyranyloxypropyl)-5-[3,4-dichlorophenl]-piperidine

The THP protected piperidinone (Intermediate 3) (13.74 g, 0.036 mol) was dissolved in tetrahydrofuran (100 ml) and 1M lithium aluminium hydride (78 ml, 2 eq) was added. The solution was stirred at 60° C. on an oil bath for 2 hours. The reaction was quenched carefully with 2M sodium hydroxide (15 ml) and water (15 ml). The aqueous phase was extracted with ethyl acetate (×2) and the combined organic phase was washed with water (×1), brine (×1) and dried (MgSO$_4$). The solvent was evaporated to provide the title compound (10.0 g, 76% yield).

$^1$H NMR (250 MHz, CDCl$_3$): δ 7.41–7.38 (2H, m) 7.17 (1H, dd, $J_1$=8.47 Hz, $J_2$=2.23 Hz) 4.46 (1H, t, J=3.51 Hz) 3.84–3.75 (1H, m) 3.69–3.56 (1H, m) 3.49–3.41 (1H, m) 3.28–3.19 (2H, m) 2.86–2.71 (2H, m) 2.12–2.05 (1H, m) 1.85–1.37 (12H, m) 1.31–1.14 (3H, m).

INTERMEDIATE 8

5-(3-Tetrapyranyloxypropyl)-5-[3,4-dichlorophenyl]-piperidine (Alternative route)

a) 4-(3-Tetrahydropyranyloxypropyl)-4-cyano-4-[3,4-dichlorophenyl]-butan-1-ol

The nitrile ester (Intermediate 2) (2.07 g, 4.84 mmol) was dissolved in tetrahydrofuran (10 ml) and cooled on a ice-bath. lithium aluminium hydride (1M, THF, 14.5 ml, 3 eq) was added over 10 minutes. The solution was then stirred at 60° C. on an oil bath for 2 hours after which it quenched carefully with sodium hydroxide (2M, 2 ml) and water (2 ml). The solution was filtered through a Hyflo™ filter and the filtrate was dried (MgSO$_4$) and evaporated to provide the title compound (1.71 g, 91% yield).

b) 5-(3-Tetrapyranyloxypropyl)-5-[3,4-dichlorophenyl]-piperidine

The amino alcohol of step (a) (1.70 g, 436 mmol) was dissolved in anhydrous dichloromethane and triphenyl phosphine (1.26 g, 1.1 eq) was added. After stirring for 5 minutes diethyl azodicarboxylate (0.73 g, 1 eq) was added and the mixture was stirred for 5 hours. The solution was diluted with water and extracted with dichloromethane (×2). The combined organic phase was washed with water (×2), brine (×1), dried (MgSO$_4$) and the solvent was evaporated. The residue was purified by flash chromatography using ethyl acetate/methanol/ammonia (gradient 100:0:0 to 90:10:0.2) as eluant to provide the title compound (1.123 g, 69% yield).

INTERMEDIATE 9

5-(3-Tetrapyranyloxypropyl)-5-[3,4-dichlorophenyl]-1-benzoylpiperidine

The THP protected piperidine (Intermediate 7) (10.0 g, 0.027 mol) was dissolved in dichloromethane (50 ml) on an ice-bath. Triethylamine (3.00 g, 1.1 eq) was added. Benzoyl chloride (4.18 g, 1.1 eq) was dissolved in dichloromethane (50 ml) and added dropwise. The reaction was allowed to warm to 23° C., stirred for 2 hours and then quenched with sodium bicarbonate and extracted with dichloromethane (×3). The combined organic phase was washed with water (×1), brine (×1) and dried (MgSO$_4$). The solvent was removed in vacuo to provide the title compound as a brown solid. This material was used without further purification.

$^1$H NMR at 353K (360 MHz, DMSO): δ 7.53 (1H, d, J=8.58 Hz) 7.50 (1H, m) 7.40 (3H, m) 7.31 (1H, m) 7.23 (2H, m) 4.41 (1H, m) 4.12 (1H, m) 3.66 (1H, m) 3.51–3.36 (5H, m) 3.22 (1H, m) 2.10 (1H, m) 1.84 (1H, m) 1.68 (2H, m) 1.56 (2H, m) 1.42 (6H, m) 1.18 (2H, m).

INTERMEDIATE 10

5-(3-Hydroxypropyl)-5-[3,4-dichlorophenyl]-1-benzoylpiperidine

The THP protected amide (Intermediate 9) (12.8 g, 0.027 mol) was deprotected by stirring with 3M hydrochloric acid in methanol (150 ml) for 2 hours. The solvent was removed in vacuo and the residue was redissolved in ethyl acetate and washed with sodium bicarbonate (×1), water (×1) and (MgSO$_4$). The solvent was evaporated to provide the title compound. This material was used without further purification.

$^1$H NMR at 353K (360 MHz, DMSO): δ 7.53 (1H, d, J=8.47 Hz) 7.49 (1H, s) 7.41 (3H, m) 7.30 (1H, m) 7.22 (2H, m) 4.18 (1H, m) 4.04 (1H, m) 3.43–3.22 (5H, m) 2.11 (1H, m) 1.81 (1H, m) 1.69–1.54 (3H, m) 1.36 (1H, m) 1.04 (2H, m).

INTERMEDIATE 11

5-(3-Methanesulfonylpropyl)-5-[3,4-dichlorophenyl]-1-benzoylpiperidine

The amido alcohol (Intermediate 10) (11.3 g, 0.029 mol) was dissolved in dichloromethane (100 ml), triethylamine (4.36 g, 1.5 eq) and then methanesulfonyl chloride (3.63 g, 1.1 eq) were added and the mixture stirred for 1 hour. The reaction was quenched with sodium bicarbonate and extracted with dichloromethane (×3). The organic layer was washed with water (×1), brine (×1) and dried (MgSO$_4$). The solvent was evaporated and the residue was purified by flash chromatography using ethyl acetate/petroleum ether (50:50 and 100:0) as eluant to provide the title compound as a gum (8.82 g, 63% yield). m/z (ES+) 470.

EXAMPLE 1

5-[3-{4,4-(N-Sulfonamidomethyl-3, 3-indolyl)piperidino}propyl]-5-[3,4-diphenyl]-1-benzylpiperidin-2-one The lactam mesylate (Intermediate 6) (0.433 g, 0.923 mmol) was dissolved in dimethylformamide (3 ml). Potassium carbonate (0.262 g, 2 eq) and 4,4-[N-sulfonamidomethyl-3,3-indolyl]-piperidine (0.268 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography using dichloromethane/methanol (gradient 100:0 to 95:5) as eluant to provide the title compound as a white amorphous solid (219 mg, 37% yield).

$^1$H NMR (250 MHz, CDCl$_3$): δ 7.42–7.02 (11H, m) 6.80 (1H, dd, J$_1$=8.45 Hz, J$_2$=2.30 Hz) 4.86 (1H, d, J=14.33 Hz) 4.39 (1H, d, J=14.33 Hz) 3.74 (2H, s) 3.56 (1H, d, J=12.76 Hz) 3.26 (1H, d, J=12.76 Hz) 2.88 (3H, s) 2.71 (2H, br.s) 2.50–2.41 (1H, m) 2.25–1.46 (13H, m) 1.08 (2H, m). m/z (ES+) 640.

EXAMPLE 2

5-[3-{4-(2-Keto-1-benzimidazolinyl)-piperidino}propyl]-5-[3, 4-dichlorophenyl]-1-benzylpiperidin-2-one The lactam mesylate (Intermediate 6) (0.336 g, 0.716 mmol) was dissolved in dimethylformamide (5 ml). Potassium carbonate (0. 198 g, 2 eq) and 4-[2-keto-1-benzimidazolinyl]-piperidine (0.175 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography (three times) using dichloromethane/methanol (gradient 100:0 to 96:4) as eluant to provide the title compound as a white amorphous solid (13 mg, 3% yield).

$^1$H NMR (250 MHz, CDCl$_3$): δ 7.42–7.20 (7H, m) 7.12–7.00 (4H, m) 6.81 (1H, dd, J$_1$=8.45 Hz, J$_2$=2.30 Hz) 4.86 (1H, d, J=14.33 Hz) 4.40 (1H, d, J=14.33 Hz) 4.30 (1H, m) 3.56 (1H, d, J=12.76 Hz) 3.26 (1H, d, J=12.76 Hz) 2.86 (2H, br.s) 2.52–2.01 (10H, m) 1.78–1.68 (4H, m) 1.60–1.47 (1H, m) 1.09 (2H, m). m/z (ES+) 591

EXAMPLE 3

5-[3-{4-Acetyl-4-phenyl-piperidino}propyl]-5-[3, 4-dichlorophenyl]-1-benzylpiperidin-2-one The lactam mesylate, (Intermediate 6) (0.437 g, 0.932 mmol) was dissolved in dimethylformamide (5 ml). Potassium carbonate (0.385 g, 3 eq) and 4-acetyl-4-phenylpiperidine hydrochloride (0.248 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography using dichloromethane/methanol (gradient 99:1 to 97:3) as eluant to provide the title compound as a white amorphous solid (220 mg, 41% yield).

$^1$H NMR (250 MHz, CDCl$_3$): δ 7.37–7.24 (11H, m) 7.08 (1H, d, J=2.18 Hz) 6.78 (1H, dd, J$_1$=8.45 Hz, J$_2$=2.18Hz) 4.86 (1H, d, J=14.31 Hz) 4.36 (1H, d, J=14.31 Hz) 3.53 (1H, d, J=12.70 Hz) 3.23 (1H, d, J=12.70 Hz) 2.49–2.38 (6H, m) 2.22–1.87 (11H, m) 1.69 (1H, td, J$_1$12.78 Hz, J$_2$=5.5 Hz) 1.48 (1 H, td, J$_1$=12.78 Hz, J$_2$=5.51 Hz) 1.03 (2H, m). m/z (ES+) 577

EXAMPLE 4

5-[3-{1-Phenyl-1,3,8-triazaspiro[4.5]decan-4-one}propyl]-5-[3, 4-dichlorophenyl]-1-benzylpiperidin-2-one The lactam mesylate (Intermediate 6) (0.420 g, 0.896 mmol) was dissolved in dimethylformamide (6 ml). Potassium carbonate (0.493 g, 4 eq) and 1-phenyl-1,3,8-triazaspiro[4.5]decan-4-one (0.231 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography using dichloromethane/methanol (gradient 99:1 to 95:5) as eluant to provide the title compound as a white amorphous solid (186 mg, 34% yield).

$^1$H NMR (360 MHz, CDCl$_3$): δ 7.39–7.23 (9H, m) 7.10 (1H, d, J=2.25 Hz) 6.87 (3H, m) 6.81 (1H, dd, J$_1$8.45 Hz, J$_2$=2.25 Hz) 4.85 (1H, d, J=14.34 Hz) 4.69 (2H, s) 4.39 (1H, d, J=14.34 Hz) 3.55 (1H, d, J=12.70 Hz) 3.26 (1H, d, J=12.70 Hz) 2.65–2.42 (6H, m) 2.23–2.12 (4H, m) 2.06–1.97 (2H, m) 1.74 (1H, td, J$_1$=12.67 Hz, J$_2$=5.02 Hz) 1.66 (2H, d, J=13.15 Hz) 1.52 (1H, td, J$_1$=12.67 Hz, J$_2$=5.02 Hz) 1.06 (2H, m). m/z (ES+) 605

EXAMPLE 5

5-[3-{4,4-(N-Sulfonamidomethyl-3,3-indolyl)piperidino}propyl]-5-[3, 4-diphenyl]1-benzoylpiperidine The amide mesylate (Intermediate 11) (0.70 g, 1.49 mmol) was dissolved in dimethylformamide (8 ml). Potassium carbonate (0.44 g, 2 eq) and 4,4-(N-sulfonamido-3,3-indolyl)-piperidine (0.48 g, 1.2 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified twice by flash chromatography using dichloromethane/methanol (gradient 99:1 and 98:2) as eluant to provide the title compound as a white amorphous solid (178 mg, 19% yield).

$^1$H NMR at 353K (360 MHz, DMSO): δ 7.54 (1H, d, J=8.47 Hz) 7.52 (1H, s) 7.42 (3H, m) 7.33 (1H, m) 7.21 (5H, m) 7.02 (1H, t, J=7.34 Hz) 4.11 (1H, br.s) 3.73 (2H, s) 3.53 (1H, d, J=13.32 Hz) 3.36 (2H, br.s) 2.98 (3H, s) 2.62 (2H, m) 2.17 (3H, m) 1.95–1.75 (5H, m) 1.64–1.54 (5H, m) 1.39 (1H, br.s) 1.07 (2H, m). m/z (ES+) 640

EXAMPLE 6

5-[3-{4-(2-Keto-1-benzimidazolinyl)-piperidino}propyl]-5-[3,4-dichlorophenyl]-1-benzoylpiperidine The amide mesylate (Intermediate 11) (0.660 g, 1.41 mmol) was dissolved in dimethylformamide (5 ml). Potassium carbonate (0.388 g, 2 eq) and 4-(2-keto-1-benzimidazolinyl)-piperidine (0.366 g, 1.2 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified by flash chromatography using dichloromethane/methanol (gradient 100:0 to 94:6) as eluant to provide the title compound as a white amorphous solid (174 mg, 21% yield).

$^1$H NMR at 353K (360 MHz, DMSO): δ 10.52 (1H, s) 7.54 (1H, d, J=8.47 Hz) 7.52 (1H, s) 7.42 (3H, m) 7.34 (1H, m) 7.24 (2H, m) 7.13 (1H, m) 6.94 (3H, m) 4.06 (2H, m) 3.53 (1H, d, J=13.46 Hz) 3.37 (2H, br.s) 2.78 (2H, m) 2.29 (2H, m) 2.17 (3H, m) 1.97–1.87 (3H, m) 1.60 (5H, m) 1.38 (1H, br.s) 1.08 (2H, m). m/z (ES+) 591

EXAMPLE 7

5-[3-{4-Acetyl-4-phenyl-piperidino}propyl]-5-[3,4-dichlorophenyl]-1-benzoylpiperidine The amide mesylate (Intermediate 11) (0.567 g, 1.21 mmol) was dissolved in dimethylformamide (8 ml). Potassium carbonate (0.333 g, 2 eq) and 4-acetyl-4-phenylpiperidine (0.270 g, 1.1 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified by flash chromatography using dichloromethane/methanol (gradient 100:0 to 98:2) as eluant to provide the title compound as a white amorphous solid (123 mg, 18% yield).

$^1$H NMR at 353K (360 MHz, DMSO): δ 7.54 (1H, d, J=8.47 Hz) 7.52 (1H, s) 7.42–7.23 (11H, m) 4.08 (1H, m) 3.52 (1H, d, J=13.37 Hz) 3.36 (2H, br.s) 2.37–2.30 (4H, m) 2.06 (5H, m) 1.95–1.85 (6H, m) 1.57 (3H, m) 1.37 (1H, br.s) 1.03 (2H, m). m/z (ES+) 577

EXAMPLE 8

5-[3-{1-Phenyl-1,3,8-triazaspiro[4.5]decan-4-one}propyl]-5-[3,4-dichlorophenyl]-1-benzoylpiperidine The amide mesylate (Intermediate 11) (0.760 g, 1.62 mmol) was dissolved in dimethylformamide (8 ml). Potassium carbonate (0.847 g, 3.8 eq) and 1-phenyl-1,3,8-triazaspiro[4.5]decan-4-one (0.270 g, 1.1 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified by flash chromatography using dichloromethane/methanol (gradient 100:0 to 98:2) as eluant to provide the title compound as a off-white amorphous solid (333 mg, 34% yield).

$^1$H NMR at 353K (360 MHz, DMSO): δ 8.29 (1H, s) 7.52 (2H, d, J=8.47 Hz) 7.41 (3H, m) 7.33 (1H, br.s) 7.23 (4H, m) 6.88 (2H, d, J=8.11 Hz) 6.78 (1H, t, J=7.28 Hz) 4.56 (2H, s) 4.15 (1H, m) 3.52 (1H, d, J=13.40 Hz) 3.38 (2H, br.s) 2.61–2.38 (6H, m) 2.19 (3H, m) 1.87 (1H, m) 1.72–1.51 (5H, m) 1.39 (1H, br.s) 1.10 (2H, m). m/z (ES+) 605

Similarly prepared was:

EXAMPLE 9

5-[3-{4,4-(1,1-Indanyl)piperidino}propyl]-5-[3,4-diphenyl]-1-benzoylpiperidine

From the amide mesylate (Intermediate 11) and 4,4-(1,1-indanyl)-piperidine.

$^1$H NMR (DMSO-d$_6$): δ 7.54 (2H, m) 7.40 (3H, m) 7.32 (1H, br.m) 7.24 (2H, m) 7.10 (4H, m) 4.06 (1H, br.m) 3.53 (1H, d, J=13.4 Hz) 3.36 (2H, br.s) 2.81 (2H, t, J=7.2 Hz) 2.49 (2H, m) 2.18–1.60 (14H, m) 1.37 (4H, m). m/z 561 (MH+, 100%).

What we claim is:

1. A compound of the formula (I)

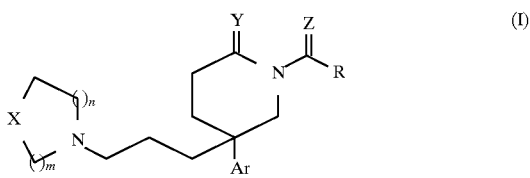

wherein m is zero, 1 or 2;

n is 1, 2 or 3, with the proviso that the sum of m+n is 1 to 4;

X represents

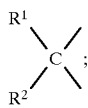

one of Y and Z represents =O whilst the other represents two hydrogen atoms;

Ar represents unsubstituted phenyl; phenyl substituted by 1, 2 or 3 substituents selected from hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy; thienyl; benzothienyl; naphthyl; unsubstituted indolyl; or indolyl substituted on the nitrogen atom by a $C_{1-4}$alkyl group;

R represents unsubstituted phenyl or phenyl substituted by 1, 2 or 3 substituents selected from hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy;

$R^1$ and $R^2$ are joined together to form a 5- or 6-membered non-aromatic ring which may contain in the ring 1 or 2 groups of the formula $NR^5$, which ring is optionally substituted by an oxo group and which ring may be substituted by, or have fused thereto, a phenyl group, wherein the phenyl ring may be substituted by 1 or 2 substituents selected from hydroxy, cyano, —C(O)$NR^3R^4$, —$NR^3R^4$, —$NR^3COR^4$, halogen, trifluoromethyl, $C_{1-4}$alkyl, —S(O)$_p$$C_{1-4}$alkyl, and —C(O)$R^3$;

$R^3$ and $R^4$ each independently represent hydrogen; unsubstituted $C_{1-6}$alkyl; $C_{1-6}$alkyl substituted by 1 or 2 substituents selected from unsubstituted phenyl, hydroxy, oxo, cyano, $C_{1-4}$alkoxy and trifluoromethyl; $C_{1-6}$alkoxy; unsubstituted phenyl; or phenyl substituted by 1, 2 or 3 substituents selected from hydroxy, $C_{1-4}$alkyl, cyano, halogen, trifluoromethyl;

or the group —$NR^3R^4$ represents a saturated or partially saturated heterocyclic ring of 4 to 7 ring atoms, which ring may optionally contain in the ring one oxygen or sulphur atom or a group selected from $NR^5$, S(O) or S(O)$_2$ and which ring may be optionally substituted by one or two groups selected from hydroxy$C_{1-4}$alkyl, $C_{1-4}$alkoxy$C_{1-4}$alkyl, oxo, $COR^6$ or $CO_2R^6$;

$R^5$ represents hydrogen, $C_{1-4}$alkyl, —S(O)$_2$$C_{1-4}$alkyl, —C(O)$R^3$, unsubstituted phenyl or benzyl;

$R^6$ represents hydrogen or $C_{1-4}$alkyl; and p is zero, 1 or 2;

or a pharmaceutically acceptable salt thereof.

2. A compound as claimed in claim 1 wherein X is

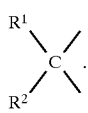

3. A compound as claimed in claim 1 wherein Ar represents unsubstituted phenyl or phenyl substituted by 1, 2 or 3 substituents selected from hydroxy, cyano, halogen, triflouromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy.

4. A compound as claimed in claim 1 wherein R represents unsubstituted phenyl or phenyl substituted by 1, 2 or 3 substituents selected from hydroxy, cyano, halogen, trifluoromethyl, $C_{1-6}$ alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy.

5. A compound as claimed in claim 1 wherein $R^1$ and $R^2$ are joined together to form a 5-membered non-aromatic ring which may contain in the ring 1 or 2 groups of the formula $NR^5$, which ring is optionally substituted by an oxo group and which ring may be substituted by, or have fused thereto, a phenyl group, wherein the phenyl ring may be substituted by 1 or 2 substituents selected from hydroxy, cyano, —C(O)$NR^3R^4$, —$NR^3R^4$, —$NR^3COR^4$, halogen, trifluoromethyl, $C_{1-4}$alkyl, —S(O)$_p$$C_{1-4}$alkyl, and —C(O)$R^3$.

6. A compound as claimed in claim 1 wherein m is 2, n is 1 and X represents:

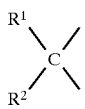

to give a group of the formula:

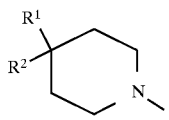

which represents a group selected from:

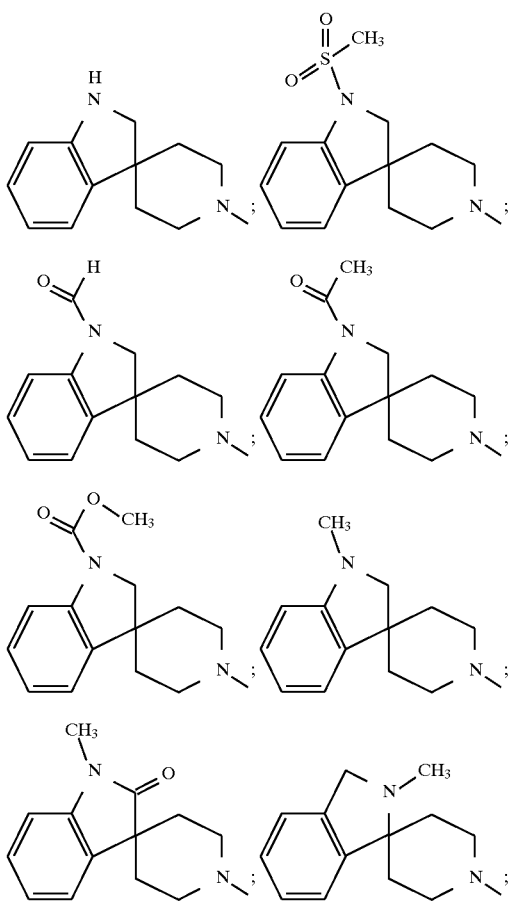

-continued

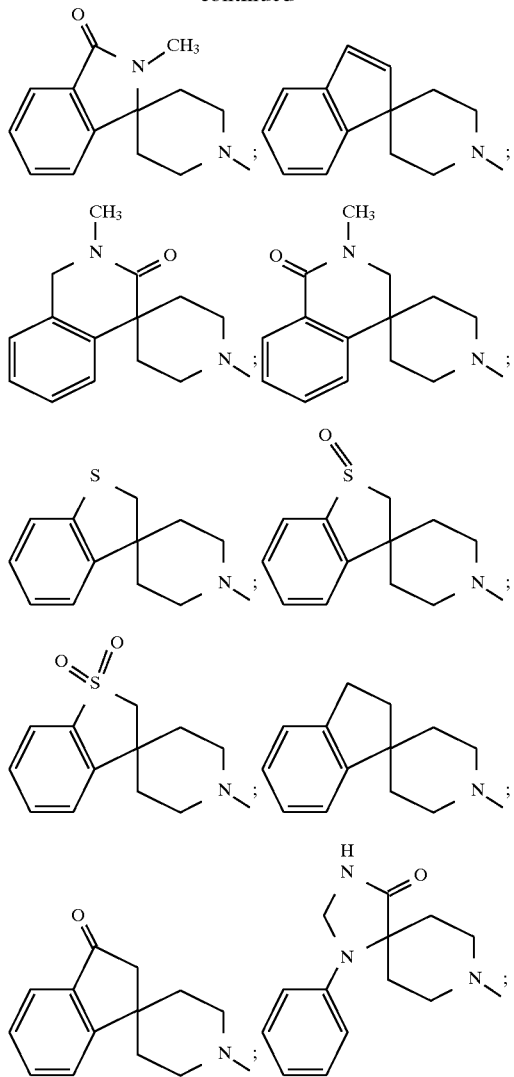

wherein each phenyl ring may be substituted by 1 or 2 substituents selected from hydroxy, cyano, —C(O)NR³R⁴, —NR³R⁴, —NR³COR⁴, halogen, trifluoromethyl, $C_{1-4}$alkyl, —S(O)$_p$C$_{1-4}$alkyl and —C(O)R³; where R³, R⁴ and p are as defined in claim 1.

7. A compound as claimed in claim 6 wherein the group represented by

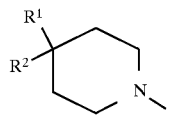

is selected from:

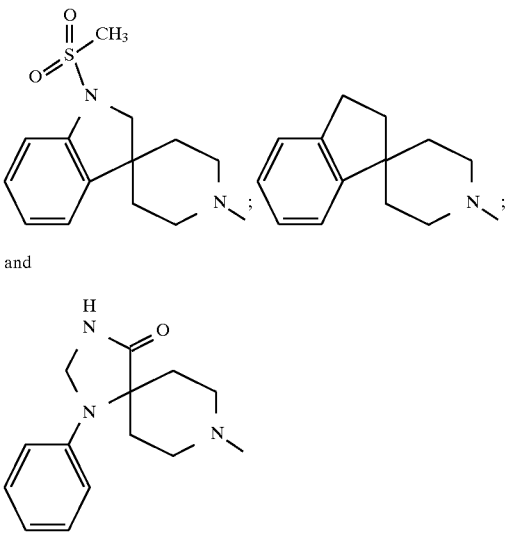

and

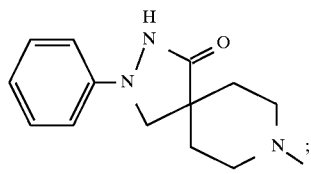

8. A compound of the formula (Ia):

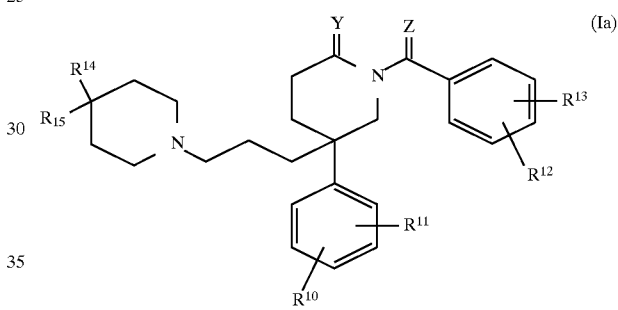

(Ia)

wherein
R¹⁰, R¹¹, R¹² and R¹³ are hydrogen or halogen atoms;
R¹⁴ and R¹⁵ are joined together to form a 5-membered non-aromatic ring which may contain in the ring 1 or 2 groups of the formula NR⁵, which ring is optionally substituted by an oxo group and which ring may be substituted by, or have fused thereto, a phenyl group, wherein the phenyl ring may be substituted by 1 or 2 substituents selected from hydroxy, cyano, —C(O)NR³R⁴, —NR³R⁴, —NR³COR⁴, halogen, trifluoromethyl, $C_{1-4}$alkyl, —S(O)$_p$C$_{1-4}$alkyl, and —C(O)R³; and
one of Y and Z represents =O whilst the other represents two hydrogen atoms;
or a pharmaceutically acceptable salt thereof.

9. A compound as claimed in claim 8 wherein R¹⁰ and R¹¹ each represent chlorine atoms, R¹² and R¹³ each represent hydrogen atoms, R¹⁴ represents unsubstituted phenyl, and R¹⁵ represents —COCH₃, or R¹⁴ and R¹⁵ are joined together to form a 5-membered non-aromatic ring which may contain in the ring 1 or 2 groups of the formula NR⁵, which ring is optionally substituted by an oxo group and which ring may be substituted by, or have fused thereto, an unsubstituted phenyl group, wherein R⁵ represents hydrogen, —S(O)₂CH₃ or phenyl.

10. A compound selected from:
5-[3-{4,4-(N-sulfonamidomethyl-3,3-indolyl) piperidino}propyl]-5-[3,4-diphenyl]-1-benzylpiperidin-2-one;
5-[3-{1-phenyl-1,3,8-triazaspiro[4.5]decan-4-one}propyl]-5-[3,4-dichlorophenyl]-1-benzylpiperidin-2-one;

5-[3-{4,4-(N-sulfonamidomethyl-3,3-indolyl)
piperidino}propyl]-5-[3,4-diphenyl]-1-
benzoylpiperidine;

5-[3-{1-phenyl-1,3,8-triazaspiro[4.5]decan-4-
one}propyl]-5-[3,4-dichlorophenyl]-1-
benzoylpiperidine;

5-[3-{4,4-(1,1-indanyl)piperidino}propyl]-5-[3,4-
diphenyl]-1-benzoylpiperidine;

or a pharmaceutically acceptable salt thereof.

11. A pharmaceutical composition comprising a compound as claimed in claim 1 in association with a pharmaceutically acceptable carrier or excipient.

12. A process for the preparation of a compound as claimed in claim 1 which comprises:

(A) reaction of a compound of formula (II)

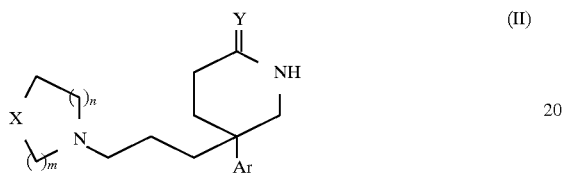

(II)

wherein Ar, X, Y, m and n are as defined in claim 1 with a compound of the formula (III)

(III)

wherein R and Z are as defined in claim 1 and LG represents a leaving group, in the presence of a base; or (B), reaction of a compound of formula (IV)

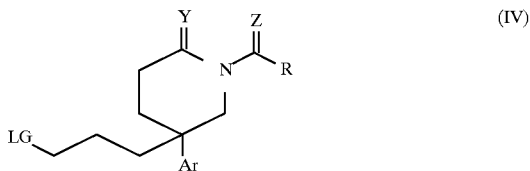

(IV)

wherein Ar, R, Y and Z are as defined in claim 1 and LG is a leaving group, with an amine of formula (V)

(V)

wherein X, m and n are as defined in claim 1, in the presence of a base;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *